(12) United States Patent
Faassen et al.

(10) Patent No.: US 8,658,687 B2
(45) Date of Patent: Feb. 25, 2014

(54) INJECTABLE FORMULATIONS CONTAINING ASENAPINE AND METHOD OF TREATMENT USING SAME

(75) Inventors: Werenfridus Adrianus Faassen, Oss (NL); Gerardus Johannes Huissen Kemperman, Oss (NL); Johannes Antonius Hendrikus van Laarhoven, Oss (NL)

(73) Assignee: Merck Sharp & Dohme Corp., Rahway, NJ (US)

( * ) Notice: Subject to any disclaimer, the term of this patent is extended or adjusted under 35 U.S.C. 154(b) by 10 days.

(21) Appl. No.: 13/378,118

(22) PCT Filed: Jun. 24, 2010

(86) PCT No.: PCT/EP2010/058960
§ 371 (c)(1),
(2), (4) Date: Jun. 5, 2012

(87) PCT Pub. No.: WO2010/149727
PCT Pub. Date: Dec. 29, 2010

(65) Prior Publication Data
US 2012/0237561 A1    Sep. 20, 2012

Related U.S. Application Data

(60) Provisional application No. 61/220,027, filed on Jun. 24, 2009.

(51) Int. Cl.
*A61K 31/40*    (2006.01)

(52) U.S. Cl.
USPC .......................................... 514/408; 424/489

(58) Field of Classification Search
USPC .......................................................... 514/408
See application file for complete search history.

(56) References Cited

U.S. PATENT DOCUMENTS

| 4,145,434 A | 3/1979 | Van Der Burg |
| 5,763,476 A | 6/1998 | Delbressine et al. |
| 2006/0084692 A1 | 4/2006 | Erik Wong et al. |

FOREIGN PATENT DOCUMENTS

| EP | 0569096 A1 | 11/1993 |
| WO | 9854186 A1 | 12/1998 |
| WO | 2006106136 A1 | 10/2006 |

OTHER PUBLICATIONS

Journal of Pharm. Sciences, (Nov. 1971) vol. 60, No. 11, pp. 1733-1736.

*Primary Examiner* — Jake Vu
(74) *Attorney, Agent, or Firm* — H. Eric Fischer; John C. Todaro

(57) ABSTRACT

The present invention provides a formulation comprising asenapine hemipamoate suspended particles, which formulation can be administered via a Depot provided by an IM injection of the formulation, and which depot does not display a particle-size dependent release rate. The present invention provides also methods of treatment using the same.

16 Claims, 12 Drawing Sheets

INJECTABLE FORMULATIONS CONTAINING ASENAPINE AND METHOD OF TREATMENT USING SAME

Cross-Reference to Related Applications

This application is the National Stage of International Application No. PCT/EP2010/058960 filed on Jun. 24, 2010, which claims the benefit under 35 U.S.C. 119(e) of U.S. Provisional Application No. 61/220,027 filed Jun. 24, 2009, each of which applications are incorporated by reference as if fully set forth herein.

FIELD OF THE INVENTION

This application discloses a novel formulation comprising asenapine hemipamoate which is suitable for depot administration of asenapine and methods of treatment using the same.

BACKGROUND OF THE INVENTION

Identification of any publication in this section or any section of this application is not an admission that such publication is prior art to the present invention.

U.S. Pat. No. 4,145,434 (the '434 patent), in Example IV therein, describes the preparation of trans-5-chloro-2-methyl-2,3,3a,12b-tetrahydro-1H-dibenz-[2,3;6,7]oxepino-[4,5c]pyrolle (known also as asenapine, see Merck index monograph no. 832), which has the structure of the compound of Formula I,

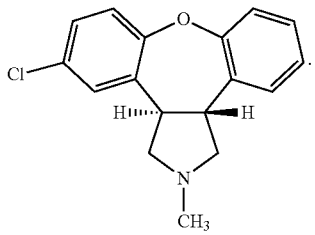

Formula I

The compound of Formula I is known to have activity in the treatment of patients afflicted with central nervous system disorders (CNS disorders). As described in the '434 patent, Col. 1, lines 45 to 50, compounds like the compound of Formula I show in general a marked CNS-depressant activity, which can be used in the treatment of states of tension, excitation and anxiety, and in the treatment of psychotic and schizophrenic conditions and show as well excellent antihistamine and antiserotonin activities. As described in U.S. Pat. No. 5,763,476 (the '476 patent), filed Mar. 9, 1995 as international application. no. PCT/EP95/00765, in Col. 1, lines 43 to 46, sublingual or buccal administration of an asenapine maleic acid salt is useful for use in treating or managing diseases including mental disorders, such as tension, excitation, anxiety, psychosis, and schizophrenia. Each of the aforementioned applications and patents are incorporated by reference as if fully set forth herein in their entirety. Treatment of bipolar disorders and associated symptoms with administration of asenapine is described in a U.S. patent application published Apr. 20, 2006 under publication no. 2006/0084692, which application is incorporated by reference as if fully set forth herein in its entirety.

Sublingual administration of a formulation comprising asenapine or a salt thereof to a patient to whom it is administered is effective in providing treatment for many CNS diseases, but requires at least regular daily administration to maintain acceptable therapeutic levels of asenapine in patients.

One serious problem to be overcome in providing effective asenapine therapy is lack of dosing compliance, particularly when the medicament is self-administered and more particularly when it must be administered daily or several times daily. Accordingly, in addressing this compliance issue, it would be preferable to have a medicament administered in a clinical setting to a patient in a form providing a therapeutically effective plasma level in the patient for a sustained period of time, thus eliminating the compliance problems associate with self-administration. This treatment modality would also require fewer dosing treatments in a given period of time.

In an effort to increase the amount of time between, doses of a medicament while maintaining a therapeutically effective plasma level of the active compound, some workers have attempted to administer some CNS active agents by intramuscular injection of a depot (Depot administration) of a composition containing the active pharmaceutical agent (API), which releases a therapeutic compound systemically over time. One example of such a dosage form reported pertains to the pamoate salt of olanzapine, an atypical antipsychotic compound unrelated to asenapine. Olanzapine pamoate has been described in U.S. Pat. Nos. 6,169,084 and 7,303,764 for use in IM administration. Depot administration of a composition containing this salt was tested in clinical trials by Eli Lilly (see for example clinical trial NCT00320489 listed on the U.S. National Institutes of Health, web site at "clinicaltrials.gov"). In these trials a depot of a formulation comprising particles of olanzapine pamoate as an active pharmaceutical agent (API) suspended in a liquid was administered by intramuscular injection (Depot administration). Initially, based on the results of these trials, the FDA declined to approve the formulation for sale citing incidents in the trials of extreme sedation and reversible coma associated with the administration of the formulation. The cause of these adverse events has not been verified, but is believed to be related to unexpectedly rapid dissolution of the suspended API in the injected depot and concomitant rapid systemic absorption of the dissolved material. Subsequently the FDA has approved this formulation for Depot injection subject to strict conditions of patient monitoring. Accordingly, the risks associated with the use of this formulation remain. As this example illustrates, the provision of a salt having apparently suitable characteristics for use in a depot formulation, for example, a pamoate salt, does not necessarily by itself provide a formulation for depot administration which is free of undesirable complications.

In depot administration of a medicament comprising a particle suspension, particle size and particle size distribution of suspended API has been observed to be a factor in the release of drug from the injected depot. This point is illustrated by the study of Miller and Fincher reported in *The Journal of Pharmaceutical Sciences*, (November 1971) Vol, 60, No. 11, pp. 1733 to 1736. In their study, Miller and Fincher observed plasma levels of phenobarbitol following IM-injections of suspensions of different fractions of classified phenobarbitol particles into dogs. Accordingly, Miller et al. prepared separate suspensions from particle fractions having a mean particle diameter of either 6.63 microns, 10.68 microns, 17.16 microns or 29.96 microns as determined using a Coulter counter. As shown in FIG. 1, plasma concentrations of phenobarbital observed by Miller et al. following depot injection of these suspensions tracked inversely with the mean particle diameter of the phenobarbital particle fraction used to prepare the suspension. This is to say that for equivalent weight percentages of API in a suspension, injection of equal amounts of API in suspensions made with particles having a smaller mean particle size provided higher $C_{max}$ in a shorter time post injection than those suspensions prepared from particle fractions having a larger mean particle size.

From the foregoing it can be seen that the attempt to provide a formulation suitable for depot administration implicates issues not addressed by merely identifying a salt form of the drug which has acceptable solubility and melting point properties. As mentioned above, depot formulations are subject to unexpected release profiles due to particle size and other factors described above.

Another aspect of the problem which can interfere with success in the provision of a formulation suitable for use in depot administration, especially in the provision of a depot formulation having extended release properties, is the stability of the active pharmaceutical ingredient (API) used in the formulation. Instability of the formulation can adversely impact the effectiveness of the formulation when subjected to the physiological environment in which it is used as well as impact the ability to store the formulation for long periods or, under ambient conditions. For example, where the API is in a crystalline form, loss of crystallinity or a change in crystalline morphology has been observed to have a profound effect on release rates from a depot injection administered using such a formulation.

As described in Published European application publication no. EP0569096, published Nov. 10, 1993 (the '096 publication), which is incorporated by reference as if fully set for herein in its entirety, pamoate salts of trans-5-chloro-2-methyl-2,3,3a12b-tetrahydro-1H-dibenz-[2,3;6,7]oxepino-[4,5c]pyrolle (asenapine, the compound of Formula I) are known, including 1:1 pamoate salt (comprising equimolar amounts of pamoic acid and asenapine free base reacted together) and, a 2:1 hemipamoate salt (comprising a 2:1 mole ratio of asenapine and pamoic acid reacted together). Published international application no. WO98/5086 (published Dec. 3, 1998, applicant Akzo-Nobel) characterizes the asenapine her salt described in the '096 publication (which is also referred to as "the Form I hemipamoate salt", as comprising a mixture of amorphous and crystalline material with a melting point of from about 167° C. to about 168° C.

The two aforementioned publications, which describe various depot formulations containing aromatic acid salts of asenapine, do not indicate that the hemipamoate mentioned therein is suitable for use in a depot formulation. The provision of asenapine salts of pamoic acid (pamoate and hemipamoate Form I) has here-to-fore not resulted in the provision of a form of asenapine which is sufficiently stable and possessed of suitable dissolution characteristics for use in a formulation intended for depot administration, particularly for use in the provision of an extended release administration from a depot provided by IM injection of the formulation.

Objectives and Summary of the Invention

In view of the foregoing, what is needed is an asenapine-containing formulation which is suitable for Depot administration of asenapine, particularly administration of a Depot which provides therapeutic plasma levels of asenapine over a prolonged period, for example, a period of at least about 2 weeks or longer. Moreover, what is needed is a method of treating diseases amenable to treatment by asenapine utilizing a formulation adapted for Depot administration. These and other objectives and/or advantages are provided by the present invention which in one aspect is a pharmaceutical formulation comprising particles of crystalline Form II of asenapine hemipamoate (defined herein) suspended in an aqueous suspending medium, wherein the particles of asenapine hemipamoate are present in the formulation in a concentration of at least about 5 mg asenapine hemipamoate/mL of formulation, more preferably the concentration is at least about 50 mg asenapine hemipamoate/mL of formulatiom more preferably the concentration is at least about in excess of 100 mg asenapine hemipamoate/mL of formulation. In some embodiments it is preferred for the concentration to be at least about 200 mg asenapine hemipamoate/mL of formulation. In some embodiments it is preferred for the concentration to be from about 50 mg asenapine hemipamoate/ml, of formulation to about 300 mg asenapine hemipamoateimL of formulation. In some embodiments it is preferred for the concentration to be from about in excess of 100 mg asenapine hemipamoate/mL of formulation to about 300 mg asenapine hemipamoate/mL of formulation, more preferably the concentration is from about 200 mg asenapine hemipamoate/mL of formulation to about 300 mg asenapine hemipamoate/mL of formulation.

In some embodiments it is preferred to prepare the formulation of the invention using particles of crystalline Form II of asenapine hemipamoate which have a $d_{50}$-value, as determined by laser diffractometry, of from about 3.5 microns to about 28 microns. In some embodiments it is preferred to provide particles of crystalline Form II of asenapine hemipamoate by micronizing precipitated crystalline material. In some embodiments it is preferred to provide particles of crystalline Form II of asenapine hemipamoate by precipitating crystals under controlled crystallization conditions. In some embodiments it is preferred to employ unclassified particulate crystalline Form II of asenapine hemipamoate. In some embodiments, it is preferred to classify particulate crystalline Form II of asenapine hemipamoate to remove particles smaller than about 0.3 microns prior to being incorporated into a formulation of the invention. In some embodiments, it is preferred to classify particulate crystalline Form II of asenapine hemipamoate to remove particles larger than about 200 microns prior to being incorporated into a formulation of the invention. In some embodiments it is preferred to classify the particle fraction to remove both particles smaller than about 0.3 microns and particles larger than about 200 microns prior to being incorporated into a formulation of the invention.

In some embodiments, preferably the aqueous suspending media used in the formulation comprises a buffer. In embodiments employing a buffer as the suspending media, preferably the buffer is a phosphate buffer. In embodiments employing a buffer, preferably the buffer has a physiologically compatible pH, more preferably it has a pH of from about pH 4 to about pH 8, more preferably the buffer has a pH of about pH 7. In some embodiments it is preferred to employ a buffer having a buffering strength of from about 0.5 mM to about 100 mM.

In some embodiments, optionally the formulation comprises also a surfactant that can act as a dispersing agent to aid in dispersing solids in the formulation, or re-dispersing the solids in the formulation after storage and settling has occurred. In some embodiments employing a dispersing agent it is preferred to use a medium chain length polyethylene glycol, for example, macrogol 3400, as a dispersing agent.

In another aspect the present invention provides a method of using the formulation of the invention in the treatment of a patient, the method comprising administering an amount of the formulation to a patient in need of asenapine therapy by intramuscular injection (IM) of a sufficient volume of the formulation to provide a depot which maintains a therapeutic plasma concentration of asenapine for a period of at least about 2 weeks, preferably from about 2 to about 4 weeks. In some patient populations it will be desirable to administer a sufficient depot volume that the patient will be provided thereby a therapeutic plasma concentration of asenapine for a period of up to 6 weeks or even up to 8 weeks.

In some embodiments, it is preferred to administer contemporaneous injections at multiple sites to form multiple depots to achieve the desired volume of the depot to provide for extended periods of therapeutic plasma concentration. In some embodiments it is preferred to inject an amount of the formulation to provide a depot volume (either as one or more than one depot) containing the equivalent to up to about 280 mg of asenapine free base to achieve the maximum desired period of maintenance of a therapeutic plasma concentration of asenapine. In some embodiments it is preferred to inject a volume of the formulation which contains an amount of Crystalline Form II of asenapine hemipamoate equivalent to from about 14 mg asenapine free base to about 280 mg of asenapine free base, more preferably, a depot volume comprising an amount of Crystalline Form II of asenapine hemipamoate equivalent to up to about 140 mg asenapine free base is administered.

Optionally, injection(s) are repeated as needed to maintain a therapeutically effective plasma concentration of asenapine. In some embodiments it is preferred to inject a volume of the formulation sufficient to provide an amount of crystalline Form II of asenapine hemipamoate which produces therapeutic plasma levels of asenapine for a period of at least two weeks, thus injections are repeated about every two weeks. In some embodiments it is preferred to inject a volume of the formulation sufficient to provide an amount of crystalline Form II of asenapine hemipamoate which produces therapeutic plasma levels of asenapine for a period of least three weeks, thus injections are repeated about every three weeks. In some embodiments it is preferred to inject a volume of the formulation sufficient to provide an amount of Crystalline Form II of asenapine hemipamoate which produces therapeutic plasma levels of asenapine for a period of at least four weeks, thus injections are repeated about every four weeks. The volume of injections will depend upon the concentration of crystalline Form II of asenapine hemipamoate present in the formulation and the aggregate volume of all of the depots administered when the formulation is administered in more than one depot formed by multiple contemporaneous injections. Accordingly, in some embodiments it is preferred to administer a volume of the formulation which provides a 2 week, 3 week, or 4 week, or longer, sustained therapeutic plasma level of asenapine. In some embodiments it is preferred to administer a volume of the formulation which will provide up to about 4 weeks of sustained therapeutic plasma level of asenapine. In some embodiments it is preferred to administer a volume of the formulation which will provide up to about 8 weeks of sustained therapeutic plasma level of asenapine. In some embodiments it is preferred to administer a volume of the formulation which will provide up to about 12 weeks of sustained therapeutic plasma level of asenapine.

The present invention further provides methods for treating a CNS disease, for example, schizophrenia or bipolar disorders. In some embodiments the method comprises administering a formulation of the invention at 2 week, 3 week, or 4 week intervals by IM injection, wherein an amount of the formulation administered provides a depot of sufficient volume to provide a therapeutically effective plasma concentration of asenapine over the selected interval. In some embodiments it is preferred to administer a volume comprising the equivalent to up to about 280 mg of asenapine free base. In some embodiments it is preferred to administer a depot volume comprising the equivalent to up to about 140 mg of asenapine freebase.

Other aspects and advantages of the invention will become apparent from the Figures and following Detailed Description.

BRIEF DESCRIPTION OF THE FIGURES

The present invention is more fully described in the following detailed description and the appended figures in which.

DETAILED DESCRIPTION OF THE INVENTION

Formulations of the present invention comprise particles of crystalline Form II of asenapine hemipamoate as an active pharmaceutical ingredient (API) suspended in an aqueous suspension medium, wherein the concentration of Crystalline Form II of asenapine hemipamoate is maintained within a particular range, described herein in greater detail.

As used herein, where particle size and particle distribution measurements are described by a numerical value, implicit in stating a numerical value is the understanding that these values reflect a precision of measurement which contemplates the normal variability experienced for a given sample when measurements are compared among different measuring techniques, different sample preparation techniques and measurements obtained by different operators of a given piece of equipment. Accordingly, as will be appreciated by those of ordinary skill in particle size and particle size distribution measurement, the stated values do not reflect absolute numerical precision but are rather indicative of particle size and particle size distribution values that are within the ordinary range of values typically observed when measuring a given sample having a particular mean particle size and particle size distribution considering the generally recognized precision and accuracy which is obtainable using a given measurement technique by those of ordinary skill in measuring particle size and particle size distribution. Accordingly, it will be understood that the values stated herein which describe a collection of particles in terms of "d-values" reflect the accuracy and precision typically available from the measuring technique employed (the details of which are described herein) and are not intended to imply greater accuracy or greater precision than is understood by those of ordinary skill in the art of particle measurement.

Figure 2B:
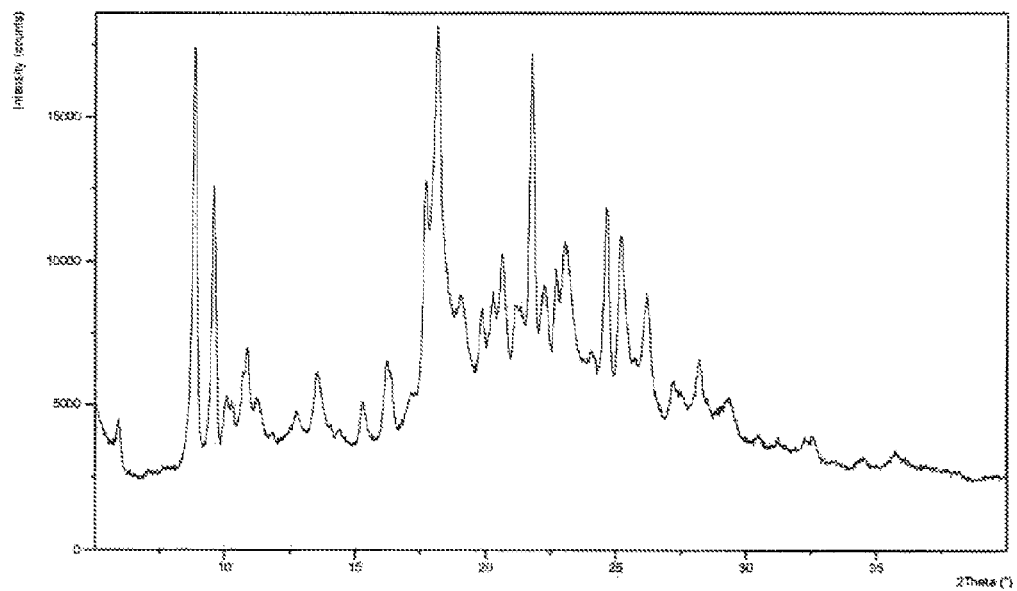
FIG. 2b presents X-Ray Powder Diffraction (XRPD) data obtained on samples of crystalline Form I of asenapine hemipamoate.
Figure 3A:
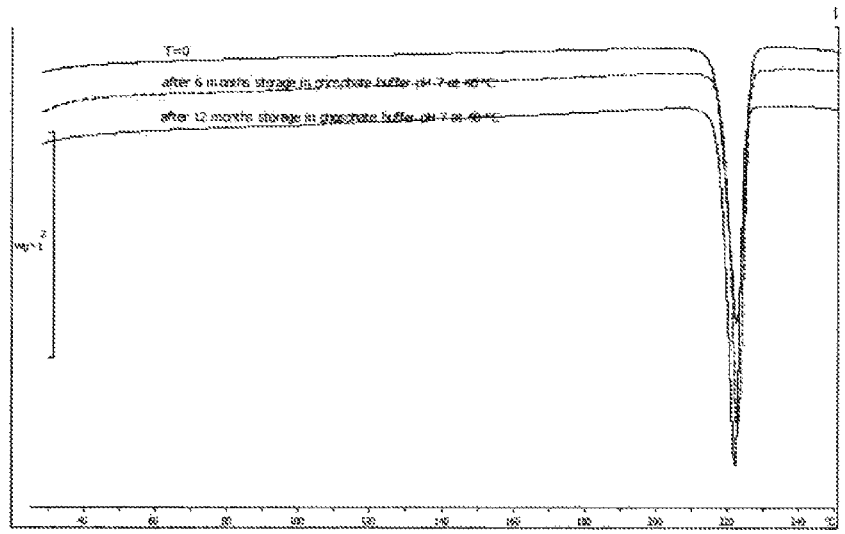
FIG. 3a presents DSC data obtained on samples of crystalline Form II of asenapine hemipamoate before and after storage in a pH 7 phosphate buffer at 30° C.
Figure 3B:
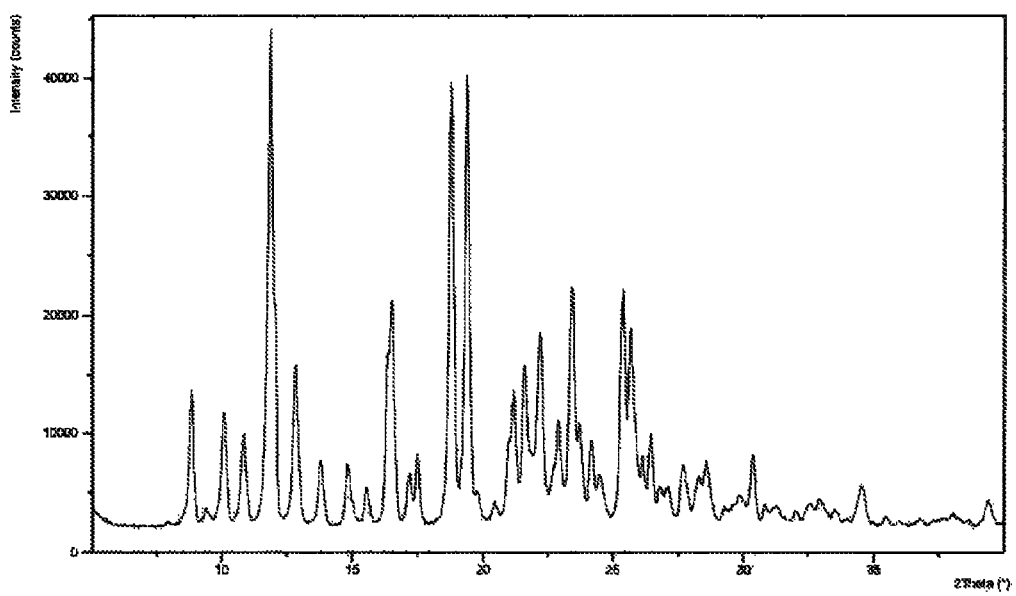
FIG. 3b presents X-Ray Powder Diffraction (XRPD) data obtained on samples of crystalline Form II of asenapine hemipamoate.

The inventors have surprisingly found that asenapine hemipamoate can be provided in crystalline Form II (described herein as "crystalline Form II of asenapine hemipamoate") which, unlike previously reported forms of asenapine hemipamoate (amorphous and Crystalline Form I), is surprisingly useful for preparing formulations suitable for depot administration. As illustrated in FIG. 3a, Crystalline Form II of asenapine hemipamoate is stable and has a melting point of about 218° C. determined by DSC analysis and, with reference to FIG. 3b, provides X-Ray Powder Diffraction (XRPD) data that indicates it is a wholly different crystalline modification of asenapine hemipamoate from any previously reported form of asenapine hemipamoate salt. For example, comparison of XRPD FIG. 2b, which is of previously reported crystalline Form I of asenapine hemipamoate, is easily distinguished from the XRPD of FIG. 3b. The procedures and results of these determinations are discussed more fully herein below. Crystalline Form II of asenapine hemipamoate has a solubility in an aqueous phosphate buffer at pH 7 of about 3 micrograms/mL.

Figure 1:
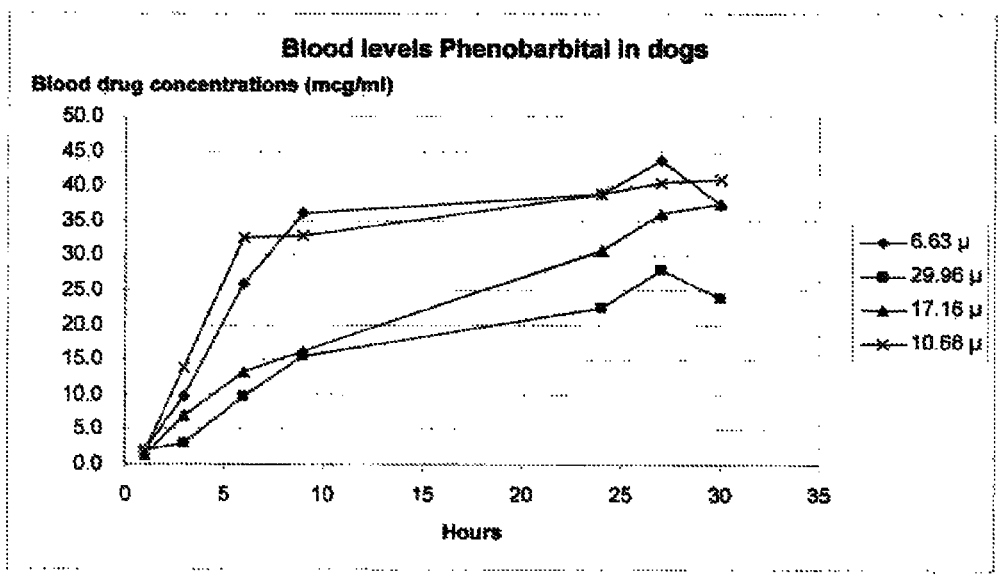
FIG. 1 is adapted from Miller et al., J. Pharm. Sci., Nov. 1971, Vol. 60, No. 11, pp 17333 to 1736, and illustrates the results of a prior art study of plasma levels of phenobarbital in dogs resulting from depot administration of suspensions having various particle sizes of Phenobarbital (see Background section above).
Figure 2A:
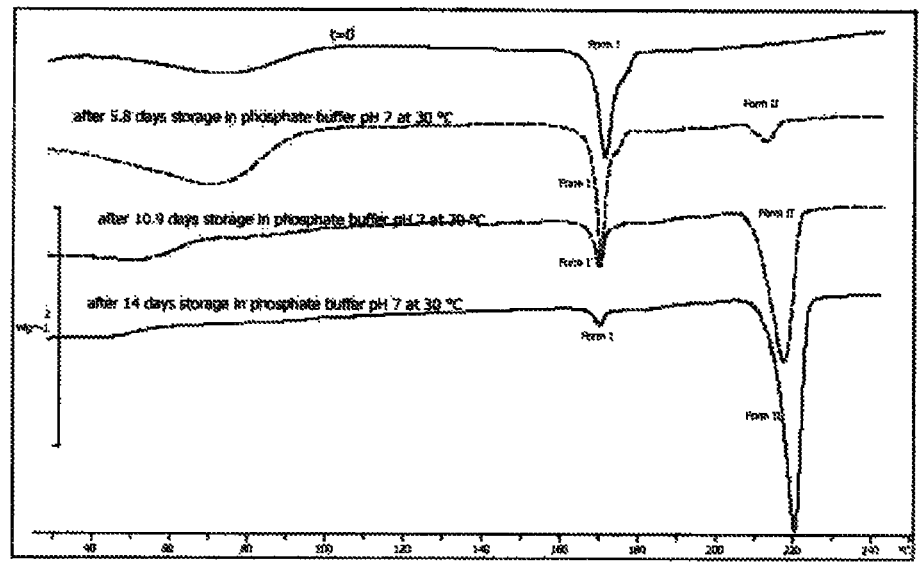
FIG. 2a presents DSC data obtained on samples of crystalline Form I of asenapine hemipamoate before and after storage in a pH 7 phosphate buffer at 30° C.

Crystalline Form I of asenapine hemipamoate, which was previously reported in published international application publication no. WO98/54186 and published European patent application No. EP0569098 (see Example II therein) yields the XRPD spectrum presented in FIG. 2b, and its differences when compared with the XRPD of Crystalline Form II of asenapine hemipamoate (FIG. 3b) are readily apparent. FIG. 2a (bottom trace) presents DSC analysis of the previously reported crystalline Form I of asenapine hemipamoate and indicates that it has a melting point of about 167° C. (centroid of the large endothermic event) with a span of from about 162° C. to about 172° C. The solubility of crystalline Form I of asenapine hemipamoate in an aqueous phosphate buffer maintained at pH 7 is about 12.6 micrograms/mL, approximately 4 times that of crystalline Form II of asenapine hemipamoate.

Figure 8A:
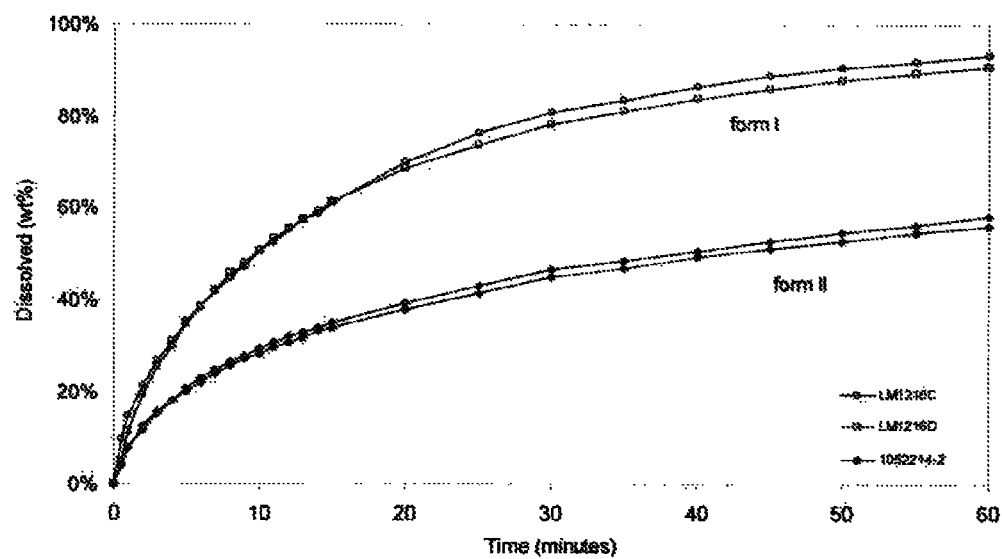
FIGS. 8a and 8b illustrate a comparison of the rate of dissolution of particles having similar particle size and size distribution of crystalline Form II of asenapine hemipamoate and of crystalline Form I of asenapine hemipamoate in a buffer solution under various test conditions.

With reference to FIG. 8a, surprisingly, particles of crystalline Form II of asenapine hemipamoate (lower traces) suspended in an aqueous dissolution medium dissolve much slower than an equivalent particle size fraction of previously reported crystalline Form I of asenapine hemipamoate (FIG. 8a, upper traces). Moreover, particles of crystalline Form I of asenapine hemipamoate suspended in a phosphate buffer at pH 7 and stored at 30° C. and 40° C. were found to convert from crystalline Form I of asenapine hemipamoate to crystalline Form II of asenapine hemipamoate based on melting point observed by DSC. With reference to FIG. 2a, the conversion of Form I to Form II was monitored by periodically taking aliquots of the stored suspension, isolating the suspended solids by filtration and drying the isolated solids at room temperature. DSC analysis was performed on the isolated, dried solids using a 10 mg sample of the solids and a Mettler DSC 822e programmed to heat at a rate of 10° C./min, from 25° C. to 250° C. The results of this study are presented in, with the result shown in the upper traces of FIG. 2a. These data clearly show that crystalline Form I of asenapine hemipamoate is slowly converted to crystalline Form II of asenapine hemipamoate. Unless noted differently, the method described for providing the DSC data show in FIG. 2 was employed in generating all of the DSC data presented herein.

Surprisingly, when this stability test was repeated starting with only crystalline Form II of asenapine hemipamoate present, the results of DSC analysis of solids recovered from a stored suspension of particles in a buffer solution indicate that under these conditions (storage at 30 and 40° C.) crystalline Form II of asenapine hemipamoate does not decompose or convert to any other crystalline form when stored for extended periods of time.

Taken together, all of the foregoing indicate that the previously reported crystalline Form I of asenapine hemipamoate is unsuitable for use in a depot formulation. Based on its solubility, the facile conversion of its crystallin, and its dissolution properties it is particularly unsuitable for use in a formulation for administering a depot to provide sustained release of therapeutic levels of asenapine. Moreover, the foregoing indicate that crystalline Form II of asenapine hemipamoate has distinct and unexpected crystalline morphology, stability properties, solubility properties, and dissolution properties, which make surprisingly well suited for use in preparing a formulation for depot administration.

The is have surprisingly found that a suspension comprising crystalline Form II of asenapine hemipamoate can provide formulations suitable for depot administration. In accordance with the present invention crystalline Form II of asenapine hemipamoate can provide a formulation suitable for administration of a depot providing sustained release of therapeutic levels of asenapine without unwanted side effects, for example, those described above for olanzapine.

The inventors have surprisingly discovered that crystalline Form II of asenapine hemipamoate can be prepared by introducing aliquots of an ethanol solution of asenapine maleate into an ethanol solution of disodium pamoate salt, and, cooling the mixture slowly (process details further described herein in the Examples which follow). The inventors have also found that this crystallization process can be carried out on a small scale to provide "seeds" which can be used to "seed" the preparation on a larger scale. Accordingly, once seeds of crystalline Form II of asenapine hemipamoate are obtained by this method, they can be employed as "seeds" to precipitate large batches of crystalline Form II of asenapine hemipamoate in a scaled-up process.

An X-Ray Powder Diffraction spectrum of crystalline Form II of asenapine hemipamoate is presented in FIG. 3b. The spectrum of FIG. 3b contains 5 most significant diffraction peaks appearing at the diffraction angle (in °2-theta) and correspondingly calculated "d-spacing" shown in Table I, below.

TABLE I

Significant Diffraction Peaks XRPD Crystalline
Form II of Asenapine Hemipamoate

| Diffraction (°2-theta) | d-spacing (Angstroms - calculated) |
|---|---|
| 11.9 | 7.5 |
| 16.5 | 5.4 |
| 18.8 | 4.7 |
| 19.4 | 4.6 |
| 23.4 | 3.8 |

With reference to FIG. 3a, a micronized sample of crystalline Form II of asenapine hemipamoate has been characterized by differential scanning calorimetry (DSC) on a Mettler DSC 822e in accordance with the above-described procedure, and was found to have a melting point of about 218° C. The melting point was taken as the centroid in the endothermic event observed within the heating range. The span of the endothermic event observed under these conditions was 213° C. to 223° C.

Asenapine maleate suitable for use in preparing crystalline Form II of asenapine hemipamoate may conveniently be prepared by following the procedures described in any of published international application publication Nos. WO2006/106136 (see for example, Schemes II and IV and Example 7 therein), WO2008/003460 (see for example, Examples 1 and 7 therein), or WO2009/087058. Each of these publications is incorporated specifically by reference as if fully set forth herein.

In accordance with the foregoing, formulations of the invention provide asenapine in a form which can be administered as a depot (Depot administration) to a patient in need of asenapine therapy. As shown below, in Example 4, when administered in a sufficient volume, preferably by intramuscular (IM) injection, administration of a depot comprising a formulation of the invention is expected to provide sustained plasma levels of asenapine in the patient without producing a "burst release" that is sometimes observed with depot injections. Accordingly, depot administration of a formulation of the invention can be carried out using a sufficient amount of the formulation to provide therapeutic plasma levels of asenapine over an extended period of time without untoward release of drug from the depot.

Figure 12:
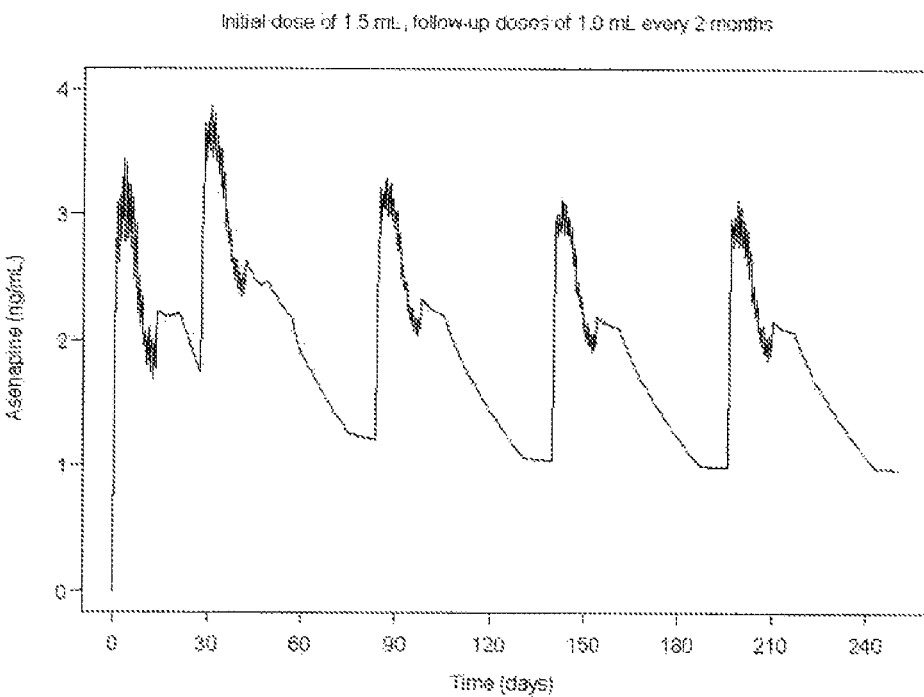
FIG. 12 illustrates a simulation of the plasma concentration levels expected in administering depot injections comprising a formulation of the invention at regular intervals.

Moreover, with reference to FIG. 12, when administered as a depot of sufficient volume at regular intervals, it will be found that a formulation of the invention provides therapeutic asenapine plasma levels in a subject to whom it is administered over an extended period, for example, two weeks, three weeks or four weeks. In some embodiments, and with some patient populations, a sufficient depot volume of the formulation is administered can be accomplished using an amount of the formulation sufficient to provide up to 8 weeks of a therapeutic asenapine plasma level.

In some embodiments, it will be useful to utilize a depot loading dose, followed by smaller depot volumes for maintenance. For example, in some embodiments it will be preferred to administer a loading dose of an amount of the formulation comprising up to about 210 mg of crystalline Form II of asenapine hemipamoate, which will be sufficient to provide therapeutic asenapine plasma levels for a period of up to about 8 weeks, followed by periodic administration of a maintenance depot in an amount comprising up to about 140 mg of crystalline Form II of asenapine hemipamoate, which will be sufficient to provide therapeutic asenapine plasma levels for additional periods of up to about 8 weeks. In some embodiments utilizing a formulation of the invention comprising 200 mg/mL of asenapine, it will be preferred to supply a loading dose comprising, for example, 1 mL of depot volume or 1.5 mL of depot volume, and administer maintenance doses at intervals thereafter which comprise a smaller volume, for example, 0.75 of depot volume, or 0.5 mL of depot volume. It will be appreciated that by continuing this administration schedule, continuous therapy can be provided to a patient. This administration is illustrated in FIG. 12, which provides a simulation of the plasma levels which can be experienced by a patient receiving a formulation of the invention in accordance with this dosing regime based on the response seen in patients and repeated administration in test animal subjects. As mentioned above, the provision of therapeutic asenapine plasma levels is useful in the treatment or management of certain CNS diseases, for example, schizophrenia.

The inventors have surprisingly found that formulations prepared using crystalline Form II of asenapine hemipamoate, wherein the concentration of crystalline Form II of asenapine hemipamoate in a formulation is maintained in according to the present invention, permit depot administration of the formulation to a subject which provides plasma levels which are independent of the particle size and particle distribution present in the aliquot of the crystalline Form II of asenapine hemipamoate from which the formulation is prepared.

Figure 4:
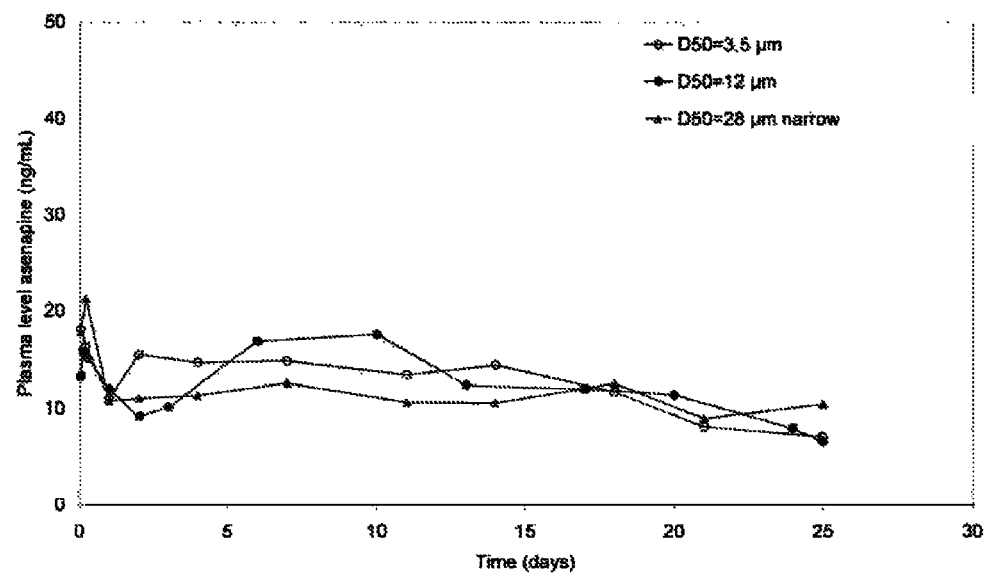
FIG. 4 illustrates plasma levels attained after Depot administration of suspensions of crystalline Form II of asenapine hemipamoate having a laser diffractometry $d_{50}$-value of 3.5 microns, 12 microns, or 28 microns.

With reference to FIG. 4, depot administration of 2 formulations of the invention, one prepared with a particle fraction having a $d_{50}$ value of 3.5 micron and 10 wt % of particle fines having a diameter of less than 0.8 micron ($d_{10}$) value of 0.8 microns) and the other prepared using a particle fraction having a $d_{50}$ value of 28 microns with almost negligible wt % of particles less than 1 micron ($d_{10}$) value of 11 microns) showed no significant differences in plasma concentration of asenapine among experimental animal subjects (details reported in Example 3, herein). This study was carried out over multiple weeks observation following depot administration. Accordingly, these data show that a formulation of the invention provides in vivo an extended release of asenapine having PK parameters which are not dependent upon the particle size or particle size distribution present in the formulation.

Although for use in a formulation of the invention it is not necessary to classify particulates into narrow particle fractions, it is preferred to prepare a formulation of the invention using a particle fraction of crystalline Form II of asenapine hemipamoate having a $d_{50}$ value, as determined by laser diffractometry, of from about 3.5 microns to about 28 microns. In some embodiments it is preferred to employ asenapine hemipamoate Form II which has been micronized to provide particulate having a $d_{50}$ value within the desired size range. Although it is not required, in some embodiments it is preferred to classify the asenapine particles used in the composition to substantially remove particles smaller than about 0.3 micron. Although it is not required, in some embodiments it is preferred to classify the particles used in the composition to substantially remove particles greater than about 200 microns. However, with reference to FIG. 4, the inventors have surprisingly found that the presence of even 10 wt. % of fines (a particle fraction having a $d_{10}$ value of less than 1 micron, for example, Sample 1 of Table 1) does not influence the plasma levels observed in experimental animal subjects to whom a depot of the formulation was administered by injection. The details of this study will be explained in greater detail in Example 3, below.

Figure 13:
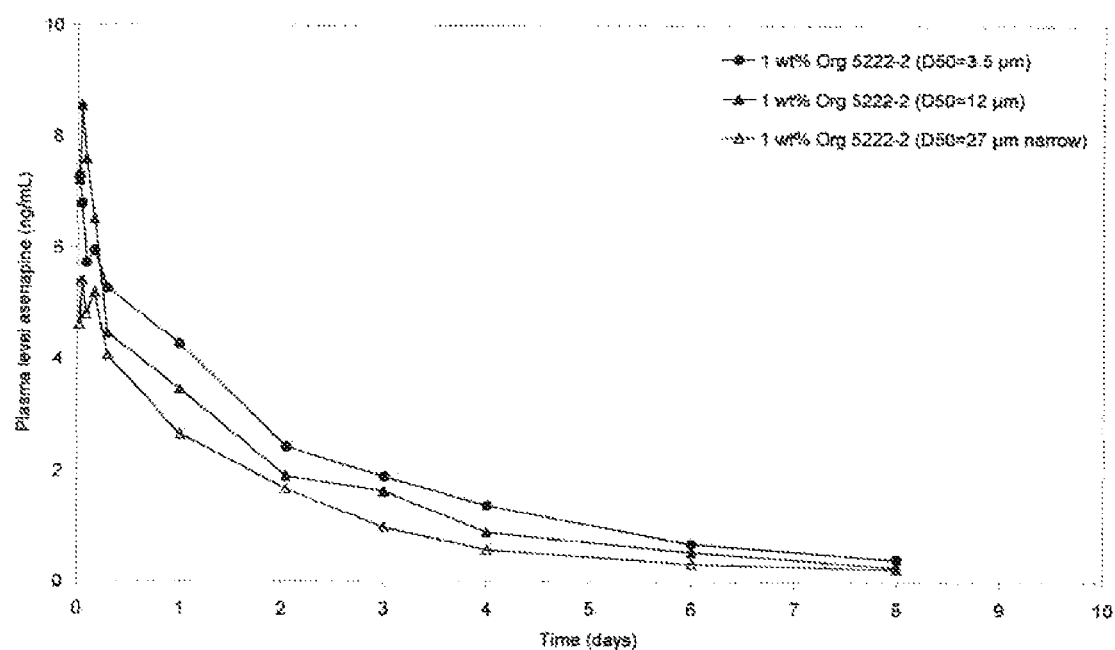
FIG. 13 illustrates plasma levels observed in test animals injected with a depot comprising a formulation of the invention comprising Form II asenapine hemipamoate particle fractions having $d_{50}$ values of 3.5 microns, 12 microns, and 27 microns, present in the formulation at a level of 1 wt %.

Preferably a formulation of the invention comprises an amount of crystalline Form II of asenapine hemipamoate sufficient to provide a concentration of at least about 10 mg of crystalline Form II of asenapine hemipamoate/mL of formulation. With reference to FIG. 13, it can be seen that formulations of the invention comprising 1 wt % of Form II of asenapine hemipamoate prepared separately using particle fractions having $d_{50}$ values of 3.5, 12, and 27 microns, when injected into a test animal in a 1.0 mL depot volume produced substantially the same plasma profile for all formulations, but the profiles suggest that when lower concentrations are employed the plasma levels produced will be differentiated with respect to the particle size employed. In some embodiments it is preferred to employ an amount of crystalline Form II of asenapine hemipamoate to provide a concentration of at least about 50 mg of crystalline Form II of asenapine hemipamoate/mL of formulation, more preferably the formulation comprises an amount of crystalline Form II of asenapine hemipamoate to provide a concentration of at least about in excess of 100 mg of crystalline Form II of asenapine hemipamoate/mL of formulation. In some embodiments it is preferred to include in the formulation an amount of crystalline Form II of asenapine hemipamoate sufficient to provide a concentration of at least about 200 mg of crystalline Form II of asenapine hemipamoate/mL of formulation. In some embodiments it is preferred to include in the formulation an amount of crystalline Form II of asenapine hemipamoate sufficient to provide a concentration of from at least about 50 mg of crystalline Form it of asenapine hemipamoate/mL of formulation to about 300 mg of crystalline Form II of asenapine hemipamoate/mL of formulation. In some embodiments it, is preferred to include in the formulation an amount of crystalline Form II of asenapine hemipamoate sufficient to provide a concentration of in excess of from about 100 mg of crystalline Form II of asenapine hemipamoate/mL of formulation to about 300 mg of crystalline Form II of asenapine hemipamoate/mL of formulation, more preferably the formulation includes an amount of crystalline Form II of asenapine hemipamoate sufficient to provide a concentration of from about 200 mg of crystalline Form II of asenapine hemipamoate/mL of formulation to about 300 mg of crystalline Form II of asenapine hemipamoatelmL of formulation. In some embodiments it is especially preferred to employ a formulation which is about 200 mg of crystalline Form II of asenapine hemipamoate/mL of formulation.

Formulations of the invention comprise particles of crystalline Form II of asenapine hemipamoate suspended in an aqueous suspending medium. The aqueous suspending medium can be sterile water alone, preferably the aqueous suspending medium comprises a buffer. In some embodiments it is preferred for the formulation to comprise crystalline Form II of asenapine hemipamoate, a buffer and a dispersing agent, and optionally one or more additional excipient which contributes to the stability of, the suspension or its utility as an injectable formulation.

In some embodiments it is preferred to prepare a formulation of the invention by combining a particle form of crystalline Form II of asenapine hemipamoate and an aqueous suspending medium with, mixing or blending until a homogeneous mixture is provided. It will be appreciated that the method of dispersing crystalline Form II of asenapine hemipamoate in the aqueous suspending medium is not critical and any suitable means of providing a homogeneous mixture of a solid suspended in a liquid can be employed.

In some embodiments where the aqueous suspending medium comprises a buffer, it is preferred to prepare the buffer to the desired pH and buffering strength and then add, with stirring, the desired amount of particulate crystalline Form II of asenapine hemipamoate. In some embodiments where the aqueous suspending medium comprises additionally a suspending agent, it is preferred to prepare the buffer, add the desired amount of suspending agent, and then add the desired amount of particulate crystalline Form II of asenapine hemipamoate. While the order of addition is not critical, in some embodiments utilizing a dispersing agent it is preferred to add the dispersing agent to the suspending medium, for example, a buffer, prior to adding particles of crystalline Form II of asenapine hemipamoate to the suspending medium.

In some embodiments where the aqueous suspending medium comprises a buffer, preferably the buffer solution provides a physiologically compatible pH, more preferably a pH of from about pH 5 to about pH 9, more preferably it provides a pH of about pH 7. In some embodiments wherein the aqueous suspending medium comprises a buffer it is preferred to employ an aqueous phosphate buffer solution as the aqueous suspending medium. It will be appreciated that other buffer materials can be employed, for example, citrate or carbonate buffers and be within the scope of the invention. It will be appreciated also that though exemplified below using a phosphate buffer prepared in a particular manner, other means of providing a buffer solution can be employed to provide a suitable aqueous suspending medium for use in preparing a formulation of the invention.

In some embodiments it is preferred to prepare a buffer by combining, for each mL of buffer prepared: up to about 60 mg of polyethylene glycol, preferably from about 5 mg of polyethylene glycol to about 60 mg of polyethylene glycol, more preferably from about 5 mg polyethylene glycol to about 30 mg of polyethylene glycol; an amount of disodium hydrogen phosphate and sodium dihydrogen phosphate that provides a phosphate moiety concentration of from about 2 mM to about 50 mM in the final buffer solution, preferably a phosphate moiety concentration of about 10 mM, wherein the ratio of each of the disodium hydrogen phosphate species and sodium dihydrogen phosphate species will depend upon the pH of the finished buffer solution; and an amount of sodium chloride sufficient to provide up to about a 0.13 M concentration of sodium chloride.

As mentioned above, in some embodiments a formulation of the invention includes one or more surfactants that have the ability to act as a dispersing agent to aid in dispersion of the asenapine hemipamoate Form II particles in the suspending medium used in preparing a formulation of the invention. In such embodiments the dispersing agent can also help to stabilize the formulation after dispersion and improve redispersion of the particles if, some particle settling has occurred after storage of the formulation. Hydrophilic polymers, for example, carboxymethyl cellulose polymers and polyethylene glycol polymers, are suitable surfactants for use as dispersing agents in a formulation of the invention. Examples of polyethylene glycol polymers which are suitable include, but are not limited to, medium weight polyethylene glycol polymers, for example, macrogols, for example, macrogol 3400, macrogol 4000, and macrogol 6000, preferably macrogol 3400.

In accordance with the foregoing, it is expected that administrating a suitable amount of a formulation of the invention comprising at least about 100 mg crystalline Form II of asenapine hemipamoate/mL of formulation to a human as a depot of suitable volume, a sustained release of asenapine that provides a constant therapeutic plasma level of asenapine of from about 1 ng/mL to about 8 ng/mL, preferably from about 1 ng/mL to about 3 ng/mL will be observed. In some embodiments it is preferred to provide an amount of formulation containing the equivalent of from about 50 mg crystalline Form II of asenapine hemipamoate, more preferably 100 mg crystalline Form II of asenapine hemipamoate, to about 300 mg of crystalline Form II of asenapine hemipamoate, more preferably at least about 200 mg of Form II of asenapine hemipamoate. In some embodiments it is preferred to provide a depot by administering the formulation by injection into the deltoid muscle of the upper arm in an amount providing from about 50 mg, more preferably 100 mg of crystalline Form II of asenapine hemipamoate, to about 300 mg of crystalline Form II of asenapine hemipamoate, preferably an amount providing about 200 mg of crystalline Form II of asenapine hemipamoate. In some embodiments it is preferred to administer a depot by injection into the gluteal muscle or into the vastus lateralis muscle an amount of the formulation comprising from about 100 mg of crystalline Form II of asenapine hemipamoate to about 300 mg of crystalline Form II of asenapine hemipamoate, preferably 200 mg of crystalline Form II of asenapine hemipamoate.

EXAMPLES

In the following examples, all reagents are USP grade article commerce unless otherwise noted.

Example 1

Preparation of Asenapine Hemipamoate and Asenapine Hemipamoate Crystalline Form II Therefrom Asenapine maleate for use in preparing crystalline Form II of asenapine hemipamoate was prepared in accordance with the procedures described in published international application No WO2008/003460 (see Examples 1 and 6 therein).

Seeds of crystalline Form II of asenapine hemipamoate were prepared by titrating aliquots of an ethanol solution of asenapine maleate into an ethanol solution of disodium pamoate and crystallizing crystalline Form II of asenapine hemipamoate therefrom. Accordingly, 201 gram of asenapine maleate prepared as described in published international application publication no. WO08/003460 was dissolved in 3.0 L of USP grade ethanol at 75° C. Disodium pamoate (108.7 g, USP grade used as received; was dissolved in 13.5 L of ethanol (USP grade) at 75° C. Aliquots of the asenapine maleate solution were added to the solution of disodium pamoate while maintaining the mixture at 75° C. After all of the asenapine maleate solution had been added, the mixture was slowly cooled to room temperature with continued stirring. The crystals which formed were collected by filtration, washed with ethanol (4 L, ambient temperature) and dried at 45° C. under house vacuum. The asenapine hemipamoate thus provided (210 gram, 87%) was examined by XPRD (FIG. 3b) and DSC (melting point 223° C. using the DSC procedure described herein) and determined to be crystalline Form II of asenapine hemipamoate.

A larger quantity of crystalline Form II of asenapine hemipamoate was prepared by seeding a solution of asenapine maleate with the seeds of crystalline Form II of asenapine hemipamoate prepared above, and then treating the seeded solution with a solution of pamoic acid in accordance with the following procedure.

An ethanol/water solvent was prepared, by combining 58 L of USP grade ethanol and 3.2 L of purified water in a vessel equipped with a stirring apparatus. The solvent was heated to about 70° C. Into this solvent was added 2703 g of asenapine maleate previously prepared (as described above) and the mixture was stirred and the temperature of the mixture maintained at about 70° C. until the solids had dissolved. The asenapine maleate solution was seeded with seeds of crystalline Form II of asenapine hemipamoate prepared in accordance with the procedure described above, and with continued stirring, a solution of 1486 g of pamoic acid dissolved in 28 L of water was added over about 1 hour, while stirring was continued and the temperature of the mixture was maintained at 70° C. The mixture was stirred at 70° C. for an additional hour during which crystals of crystalline Form II of asenapine hemipamoate were formed. After 1 hour of stirring, the mixture was cooled to ambient temperature (about 20° C.) by removing the heat source and allowing the batch to cool with stirring. Stirring was continued for an additional 16 hours. At the end of 16 hours, the precipitated crystals were recovered by filtration, washed with water at ambient temperature and dried at 45° C. under house vacuum. The identity and purity of the crystalline material produced was confirmed by DSC, which shows a sharp endotherm at 223° C., and by XRPD, which produces a spectrum conforming with the reference spectrum (FIG. 3b) for crystalline Form II of asenapine hemipamoate.

Example 2

Preparation of Injectable Composition Comprising Crystalline Form II of Asenapine Hemipamoate A phosphate buffer was prepared by placing into a vessel equipped with a mechanical stirring apparatus 1000 g of sterile water, 30 g of macrogol 3400, 1.18 g of disodium hydrogen phosphate, 0.47 g of sodium dihydrogen phosphate, and 7.6 g of sodium chloride. The vessel was stirred for one hour at ambient temperature (about 20° C.), until dissolution was complete. After all of the contents had dissolved, the pH of the buffer was adjusted by adding aliquots of 1M aqueous phosphoric acid and 1M aqueous sodium hydroxide as needed (with aliquots of the buffer being withdrawn and tested using a standard laboratory pH meter after the addition of each aliquot) until the buffer attained a pH of 7.0.

Aliquots of crystalline Form II of asenapine hemipamoate, prepared in Example 1, above, were micronized and classified into fractions having various $d_{50}$ values as determined by laser diffractometry using a Malvern particle sizer. Diffractometry was performed on samples prepared by adding 20 mg of the crystalline Form II of asenapine hemipamoate sample to be measured to 1 mL of a dispersing medium comprising an aqueous 0.05 wt. % Tween 80 solution, and adding a suitable amount of the dispersion to the apparatus measuring vessel which contained a 0.05 wt. % Tween 80 aqueous solution saturated with asenapine hemipamoate. Measurements were taken in accordance with the manufacturers operating instructions.

Using this method, the following characteristics were measured on three different particle fractions obtained by micronizing samples of crystalline Form II of asenapine hemipamoate (Table II).

TABLE II

| Sample No. | Particle Size Analysis (d values given in microns) | | |
|---|---|---|---|
| | $d_{10}$ | $d_{90}$ | $d_{50}$ |
| 1 | 0.8 | 11.9 | 3.5 |
| 2 | 1.45 | 56.9 | 12 |
| 3 | 11 | 51.6 | 28 |

Figure 5:
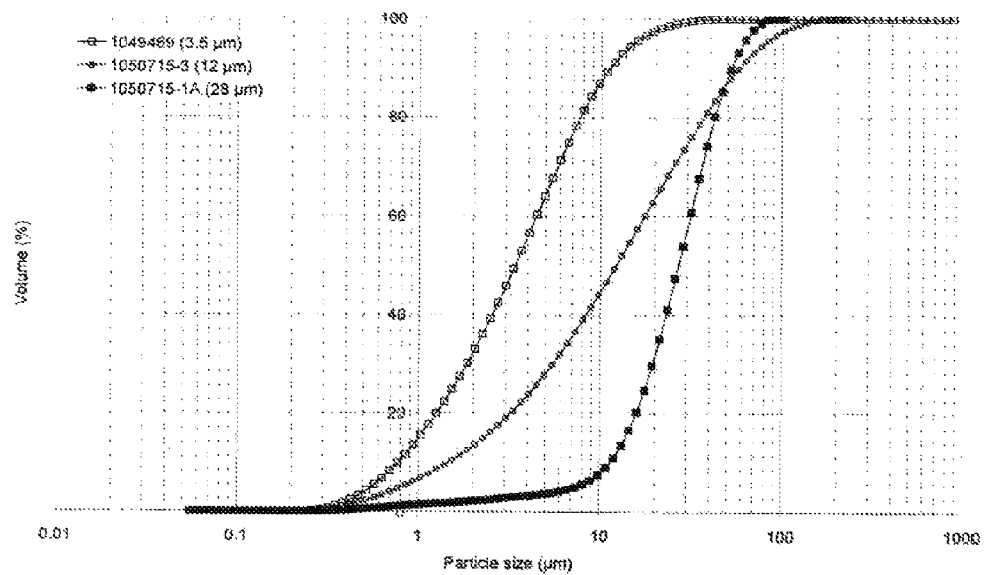
FIG. 5 graphically presents the particle size distribution in classified particle fractions having $d_{50}$-values (measured by laser diffractometry) of 3.5 microns, 12 microns, or 28 microns.

As used herein, the term "$d_{50}$" means a value representing the particle size wherein half of the sample weight comprises particles smaller than $d_{50}$ and half of the sample weight comprises particles larger than $d_{50}$. In a similar manner, $d_{10}$ is the value representing the particle size wherein 10% of the particles in the sample are smaller than $d_{10}$, and $d_{90}$ is the value wherein 90% of the particles in the sample are smaller than $d_{90}$. Accordingly, sample 1 comprises relative small particles, sample 2 comprises intermediate size particles, and sample 3 comprises large particles, as reflected by their relative $d_{50}$ values. The particle fractions described in Table 1 are referred to herein further as sample 1 ($d_{50}$=3.5 micron), sample 2 ($d_{50}$=12 micron), and sample 3 ($d_{50}$=28 micron). FIG. 5 further illustrates the particle size and particle size distribution found in these samples.

Into each of three vessels equipped with a mechanical stirrer was placed a 4800 mg aliquot of the buffer prepared above. A 1200 mg aliquot of each of particulate samples 1, 2, and 3 was weighed out. Into each vessel containing the buffer solution was added, with stirring, one of these 1200 mg aliquots, providing a formulation of the invention made from each of the particle fractions characterized, each of which formulation had a concentration of 215 mg of crystalline Form II of asenapine hemipamoate/mL of formulation.

Example 3

In Vivo Studies of Depot Administration of Asenapine Hemipamoate Composition Using Rabbits Each of the formulations prepared in Example 2 were administered to a series of experimental animal subjects (New Zealand white rabbits) as a depot injection. A depot of 1 mL volume of the formulation selected was administered into the left limb of the subject. At time intervals following injection, blood samples were collected from the subject's ear artery in 0.03 mL of 0.2M EDTA, Samples were collected at 1, 3, and 6 hours post injection, then 1, 2, 3, and 6 days post injection, then on days 10, 13, 17, 20, 24 and 25. Once collected, blood samples were centrifuged for 2 min. at room temperature (125,000 N/kg). Plasma samples thus obtained were analyzed by LC/MS after adding an internal standard. The asenapine and internal standard were isolated from the sample by solid phase extraction. The extracted components were separated by liquid chromatography in accordance with published methodology and the eluent was conducted to a triple quadrapole mass spectrometer which employed electrospray ionization in multi-reaction monitoring mode to determine asenapine content. The results of this study are presented in FIG. 4, which shows that plasma levels of asenapine observed in experimental animal subjects is approximately the same for each of the formulations studied, designated by the $d_{50}$ value of the particle fraction which was employed in preparing each formulation studied. The particle fraction used in preparing each of the formulations studied provided differing $d_{50}$ values and different particle size distributions, as shown in FIG. 5. Accordingly, these data indicate that the release rate of asenapine provided by a depot of a formulation of the invention is independent of the mean particle size or particle size distribution used to prepare the formulation. These studies indicate also that a composition of the invention can be employed to provide acceptable therapeutic levels of asenapine without untoward release of asenapine to a patient to whom it is administered.

It be appreciated from FIG. 5 that the formulation prepared from the Sample 1 particle fraction contained 10 wt. % fines (particles less than 1 micron, in the case of Sample 1, $d_{10}$ was measured to be 0.8 microns). However, the information presented in FIG. 4 demonstrates that even this loading of fines, depot administration of a formulation of the invention does not result in a release profile which is particle-size dependent.

Figure 9A:
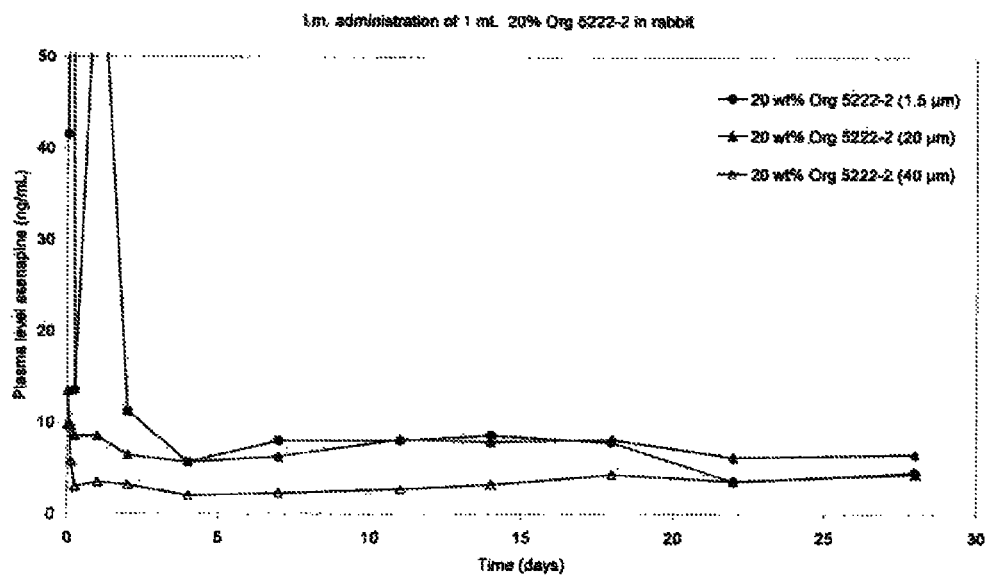
FIGS. 9a to 9c illustrate plasma concentration observed after IM injection of New Zealand White Rabbits with a 1 mL depot comprising 5 wt % or 20 wt % asenapine hemipamoate Form II.
Figure 9B:
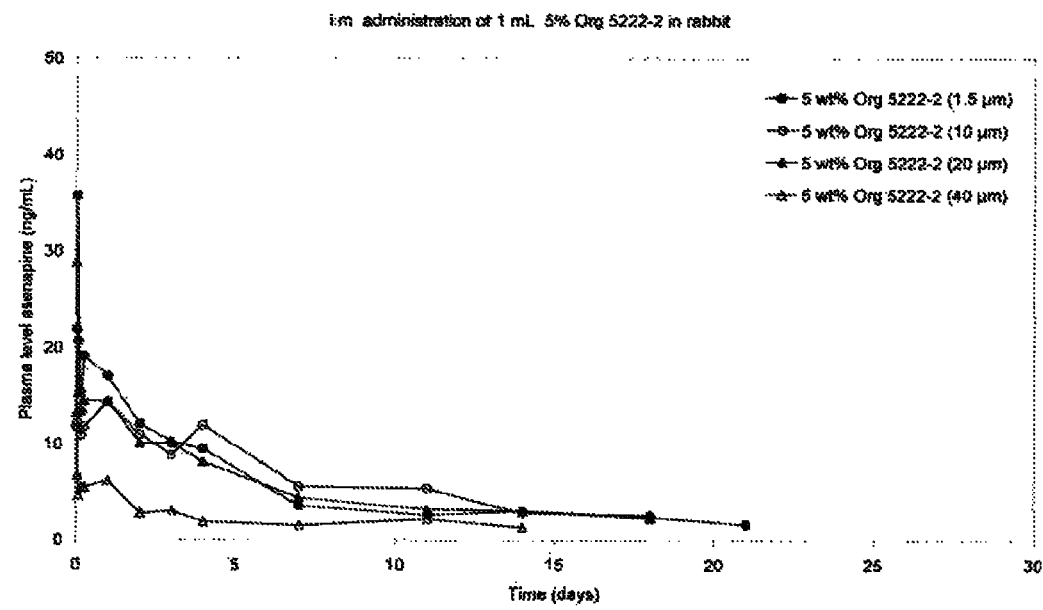
Figure 9C:
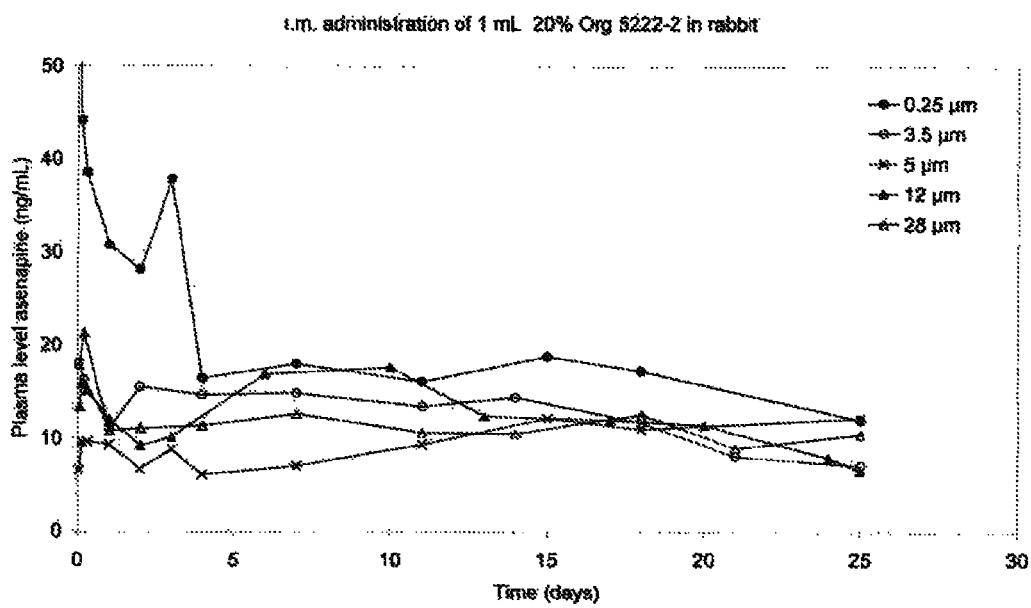
Figure 9D:
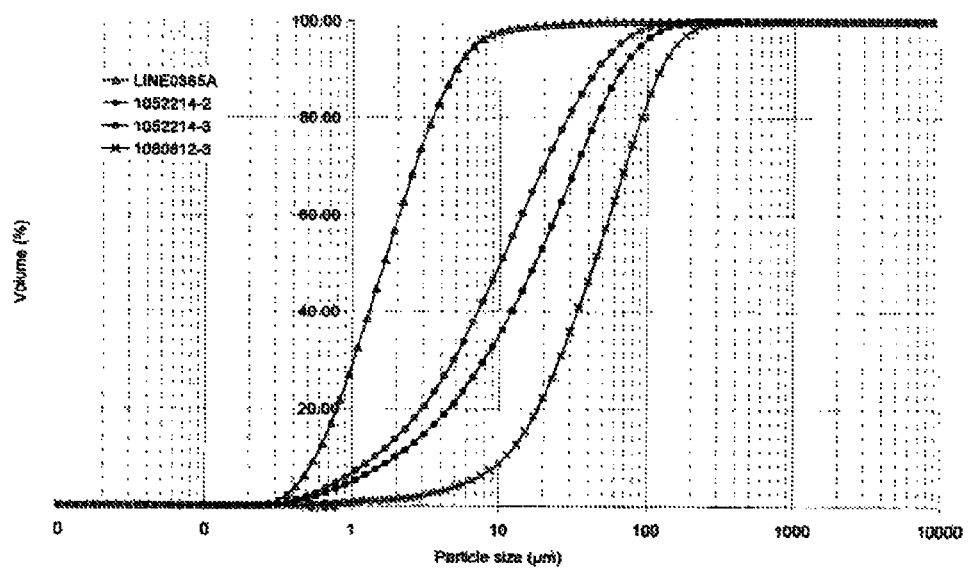
FIG. 9d illustrates the particle size distribution in the particle fractions used in providing the data in FIGS. 9a to 9c.

With reference to FIGS. 9a to 9c, additional studies were conducted using New Zealand White rabbits using the methodology described above. Accordingly, test subjects were administered an IM injection to provide a depot comprising a suspension of asenapine hemipamoate Form II prepared as described above using particulate API having: (i) a mean particle size of 1.5 microns, 20 microns, or 40 microns and a concentration of 20 wt % (FIG. 9a); (ii) a mean particle size of 1.5 microns, 10 microns, 20 microns, or 40 microns and a concentration of 5 wt % (FIG. 9b); and (iii) a mean particle size of 0.25 microns, 3.5 microns, 5 microns, 12 microns, and 28 microns and a concentration of 20 wt % (FIG. 9c).

With reference to FIG. 9a through 9d, these data indicate that at 20 wt % concentration, formulations of the invention comprising API particle fractions having less than about 10 vol % particles of less than 1 micron and a $d_{50}$ value of 28 microns or less yields a release profile that provides a consistent plasma concentration of asenapine regardless of the $d_{50}$ value of the particle fraction employed. These data indicate also that at a 5 wt % concentration, formulations of the invention comprising API particle fractions having less than about 10 vol % particles of less than 1 micron and exhibiting a $d_{50}$ value of greater than 1.5 microns and less than about 40 microns provide a consistent release profile across the range of formulations tested that yields a sustained plasma concentration of asenapine consistent with the provision of a therapeutic level of asenapine.

As can be seen in FIGS. 9c and 9a, particle fractions yielding, small $d_{50}$ values (e.g. 0.25 microns, 9c) or which have a large "fines" content (10 vol % or greater of particles with less than 1 micron particle size (e.g., 1.5 micron, 9a) tend to exhibit a "bursting effect" (also termed a "Burst Release") upon injection, and are accordingly unacceptable for use as a formulation for depot administration of asenapine.

Figure 10:
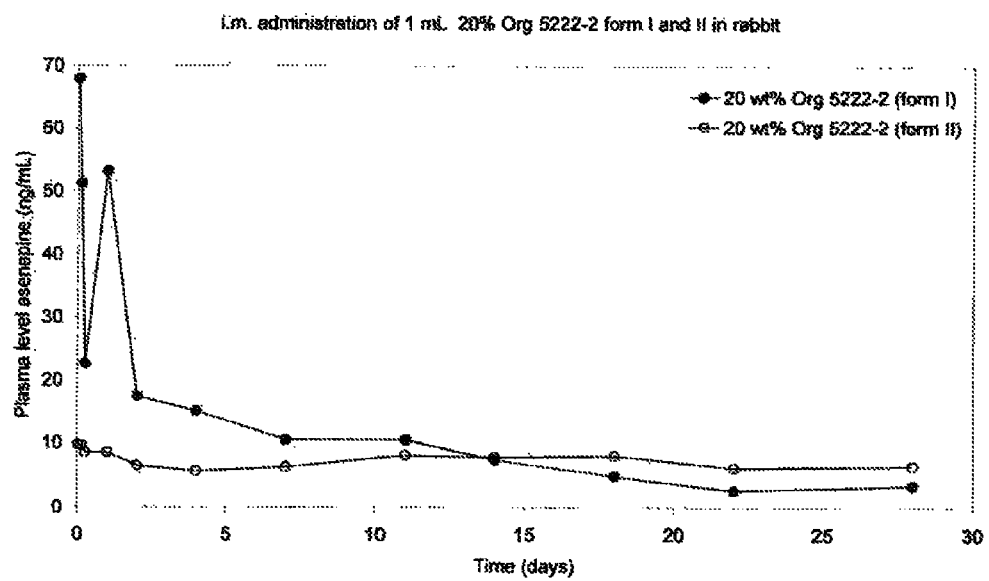
FIG. 10 illustrates a comparison of plasma concentration observed after IM injection of New Zealand White Rabbits with a 1 mL depot comprising 20 wt % asenapine hemipamoate Form I and Form II.

In additional animal studies, and with Reference to FIG. 10, using the same procedures described above, suspensions comprising 20 wt % of asenapine hemipamoate of Form I (mean particle size of 20 micron) and Form II (mean particle size 16 micron) were prepared. Aliquots of each suspension were administered as a 1 mL IM injection to New Zealand White rabbits using the same procedure described above. Plasma levels of asenapine were determined using the above-described procedure. As can be seen from FIG. 10, this illustrates that Form I of asenapine hemipamoate is unsuitable for use in providing a controlled release of asenapine in that it exhibits an undesirable "burst release", e.g. high initial plasma levels in the first week after administration in comparison to the plasma levels provided by the depot comprising Form II asenapine hemipamoate. Accordingly, formulations prepared in this manner from crystalline Form I asenapine hemipamoate are unsuitable for use in depot administration.

Example 4

Figure 11:
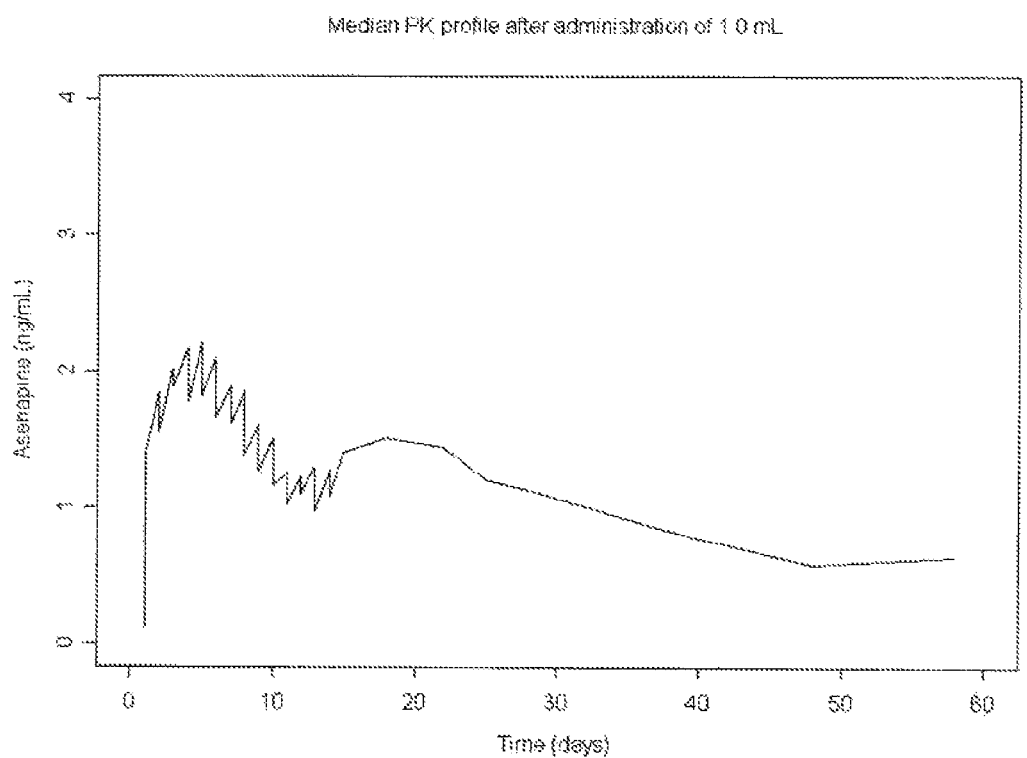
FIG. 11 illustrates median plasma concentrations observed after IM injection of patients with a 1.0 mL depot comprising 20 wt % asenapine hemipamoate Form II.

In Vivo Study of Depot Administration of Asenapine Hemipamoate Composition in Patients Formulations of the invention were studied in human patients diagnosed with stable chronic schizophrenia. Using the same procedure described above, a suspension was prepared comprising 20 wt % of crystalline Form II of asenapine hemipamoate. The Form II particle fraction employed to prepare the suspension yielded a $d_{10}$ value of 3 microns, a $d_{90}$ value of 27 microns and a $d_{50}$ value of 10 microns. An injection of 1.0 mL volume of the suspension was administered in the deltoid muscle of the upper arm by inserting the needle in the thickest part of the deltoid muscle at a 90 degree angle to the skin, followed by aspiration for 5 to 10 seconds, followed by injection of the depot over a 10 second interval. The plasma concentration of asenapine provided by the depot was observed using the above-described procedure. The results of this study are presented in FIG. 11 which shows that the composition can provide a controlled release of asenapine over a period of about 4 weeks.

It will be observed that by changing the injection volume used to provide the depot different plasma levels can be obtained.

Example 5

Figure 6:
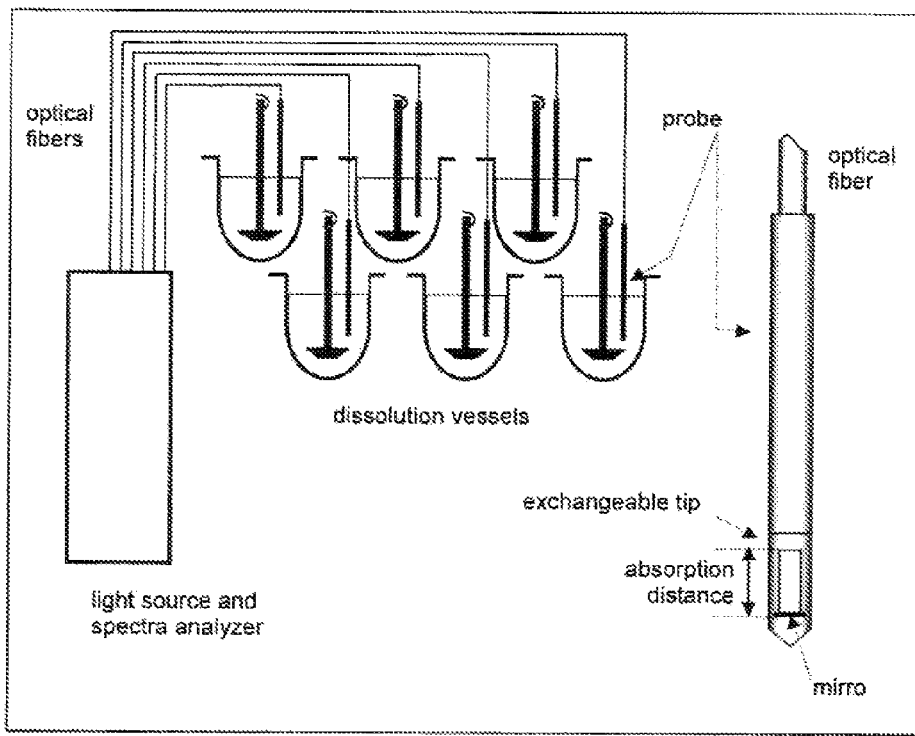
FIG. 6 schematically presents the dissolution system used to study the in vitro dissolution behavior a crystalline Form II of asenapine hemipamoate particles.
Figure 7A:
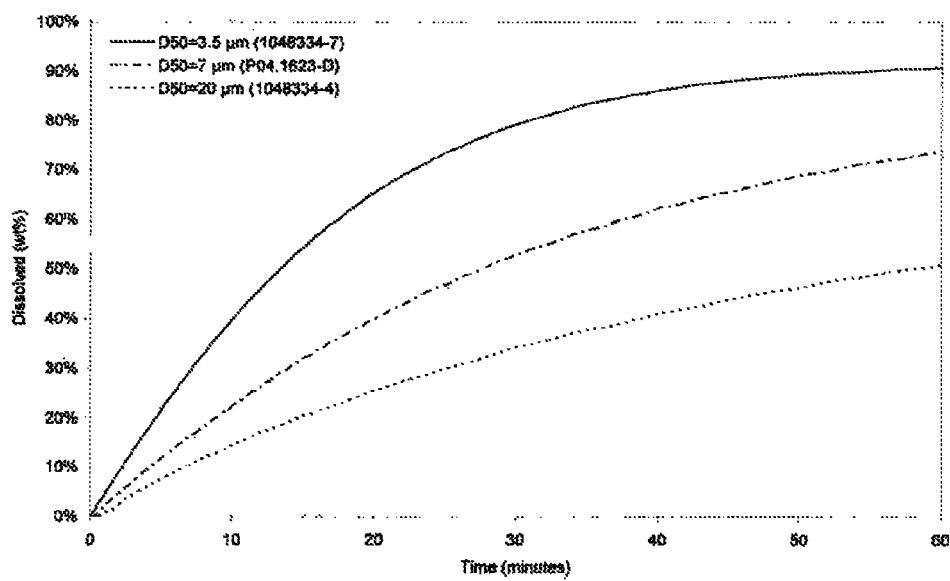
FIG. 7a-7d illustrate the rate of dissolution of particles of crystalline Form II of asenapine hemipamoate in a buffer solution under various test conditions.
Figure 7B:
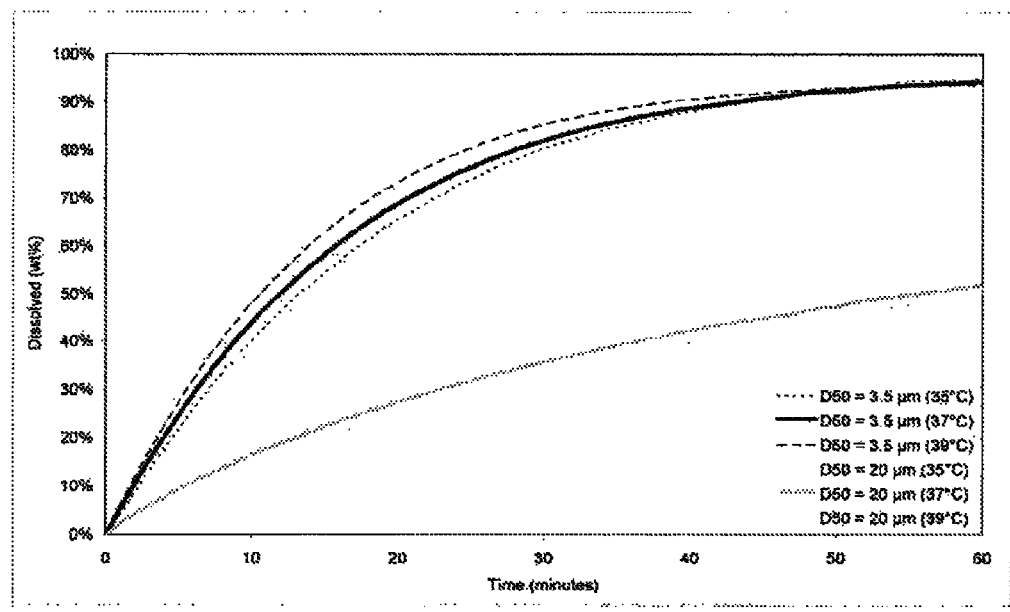
Figure 7C:
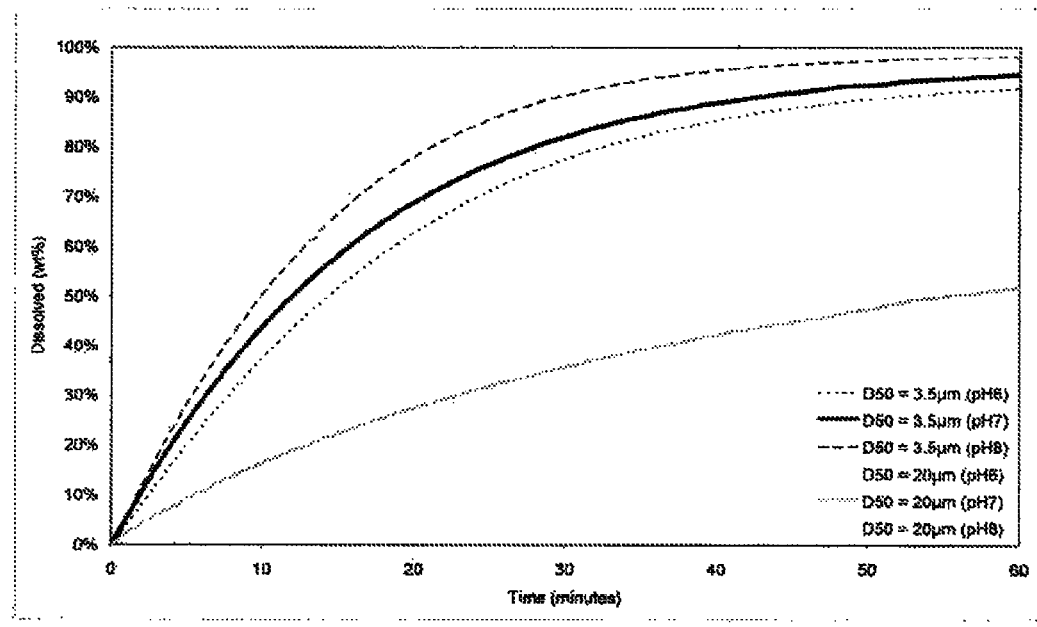
Figure 7D:
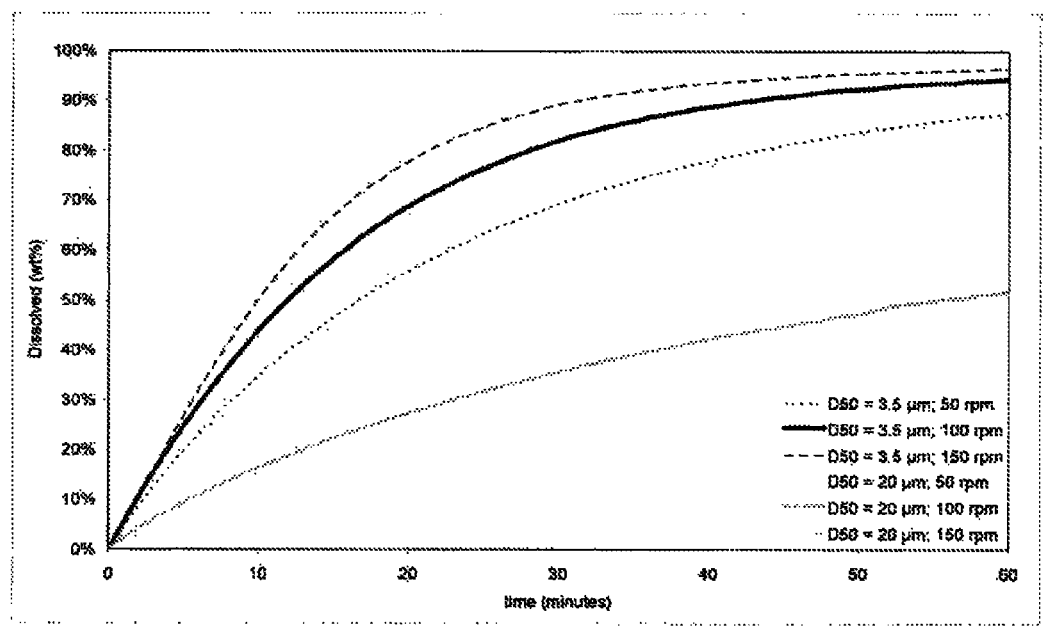
Figure 7E:
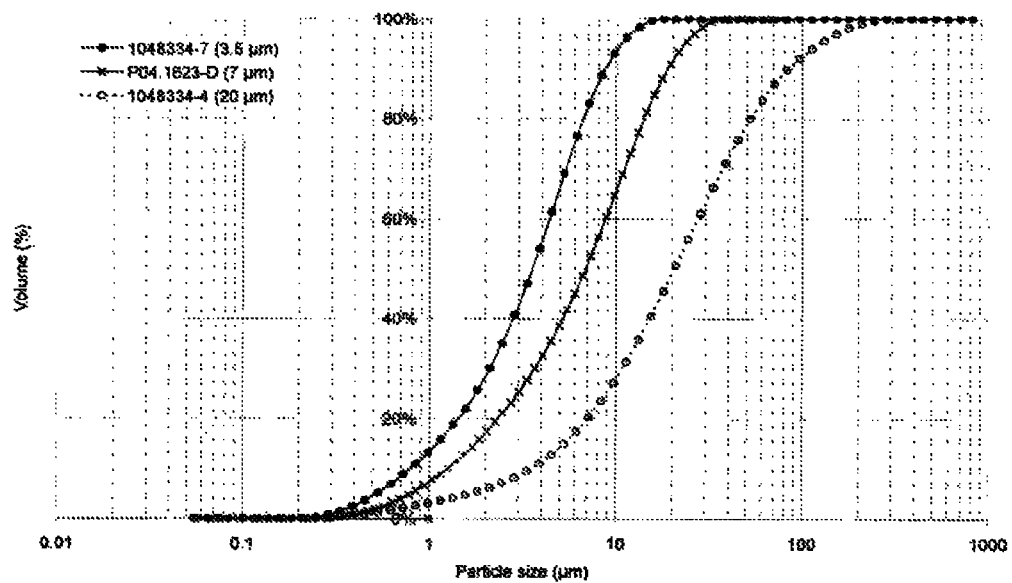
FIG. 7e illustrates the particle size distribution of the fractions used in providing the data in FIGS. 7a to 7d.

In Vitro Studies of Dissolution of Selected Particle Fractions of Crystalline Form II of Asenapine Hemipamoate In vitro studies of the dissolution behavior of particle fractions comparable to each of those reported in Table II above were conducted in a USP paddle stirring dissolution apparatus (see FIG. 6). To carry out these studies, particle, fractions of crystalline Form II of asenapine hemipamoate having $d_{50}$, values of 3.5 microns, 7 microns, and 20 microns respectively, (see FIG. 7e) were obtained and placed into one of the dissolution vessels of the apparatus. Prior to charging a dissolution vessel with an aliquot of particles, each of the vessels was filled with 1 L of phosphate buffered saline (10 mM, adjusted to pH 7.0) and fitted with a probe that contained a mirror and optical arrangement in its tip defining a fixed sample path. Each probe was optically connected to a central light source and detector permitting real-time photometric monitoring of the concentration of asenapine in solution as dissolution proceeded during the investigation. Using this system the investigators were able to observe over time the rate of dissolution under standard conditions and compare the dissolution behavior of the various particle fractions as selected variables (temperature, paddle speed, pH) were altered in the dissolution apparatu.

The particle fractions were prepared for use in the apparatus by dispersing the sample (20 mg) in 1 mL of an aqueous solution comprising 3 wt. % macrogol 3400, 0.118 wt. % of disodium hydrogen phosphate, 0.047 wt. % sodium dihydrogen phosphate and 0.76 wt. % sodium chloride. Each determination was carried out by adjusting the apparatus to the desired dissolution conditions (temperature, paddle speed, pH of dissolution media) and injecting 50 microliter of the selected crystalline Form II of asenapine hemipamoate dispersion (equivalent to 1 mg of crystalline Form II of asenapine hemipamoate) into a dissolution vessel filled with the desired dissolution medium. Asenapine hemipamoate concentration in the dissolution medium was monitored optically using the probe system described above during the course of the dissolution. The results of these investigations are reported in FIGS. 7a through 7d, which illustrate the dissolution behavior of various fractions of the crystalline Form II of asenapine hemipamoate suspensions under various test conditions. As can be seen from the FIG. 7c (observing the dissolution behavior of suspensions of particle fractions having a $d_{50}$ value of either 3.5 microns or 20 microns) variation of the dissolution medium pH (from pH 6 to pH 8) does not significantly vary the rate of dissolution of a given particle fraction, that is, neither the 3.5 micron fraction nor the 20 micron fraction appreciably change their dissolution rate with variation in the pH of the dissolution medium. In the same manner, with reference to FIG. 7d, the dissolution behavior observed for a given particle fraction is also reasonably insensitive to variation in the paddle speed of the apparatus (50 rpm to 150 rpm). Moreover, with reference to FIG. 7b, the dissolution behavior observed, for a given particle fraction is reasonably insensitive to variation in temperature of the dissolution medium (35° C. to 39° C.). However, with reference to FIG. 7a, when the dissolution rate of various particle fractions are compared under the same conditions, it was observed that the rate of particle dissolution is greatly influenced by the $d_{50}$ value of the particle fraction studied. These results indicate that a depot administration of asenapine hemipamoate prepared by suspending an unclassified particle fraction in a carrier could result in non-linear release of asenapine from the depot due to the faster dissolution rate of small particles in comparison with the slower dissolution rate of large particles.

The above-described in vitro testing methodology was used to compare the dissolution of crystalline crystalline Form I of asenapine hemipamoate hemipamoate (as precipitated) and crystalline Form II of asenapine hemipamoate (as precipitated). Accordingly, 20 mg of a particle fraction of crystalline Form I of asenapine hemipamoate having a $d_{50}$ value of 19 microns, a $d_{90}$ value of 41 microns and a $d_{10}$ value of 3 microns was dispersed into 2 mL of a polysorbate 80 solution. An aliquot of 100 microliter of the dispersion was introduced into dissolution medium contained in a paddle stirring apparatus as described above. For these tests the dissolution vessels of the apparatus were filled with 1 L of phosphate buffered saline (10 mM, adjusted to pH 7.0). The temperature of the dissolution medium was maintained at 37° C. and the apparatus paddle speed was set at 100 RPM. The dissolution results for the crystalline Form I of asenapine hemipamoate sample are shown in the upper trace of FIG. 8a.

Figure 8B:
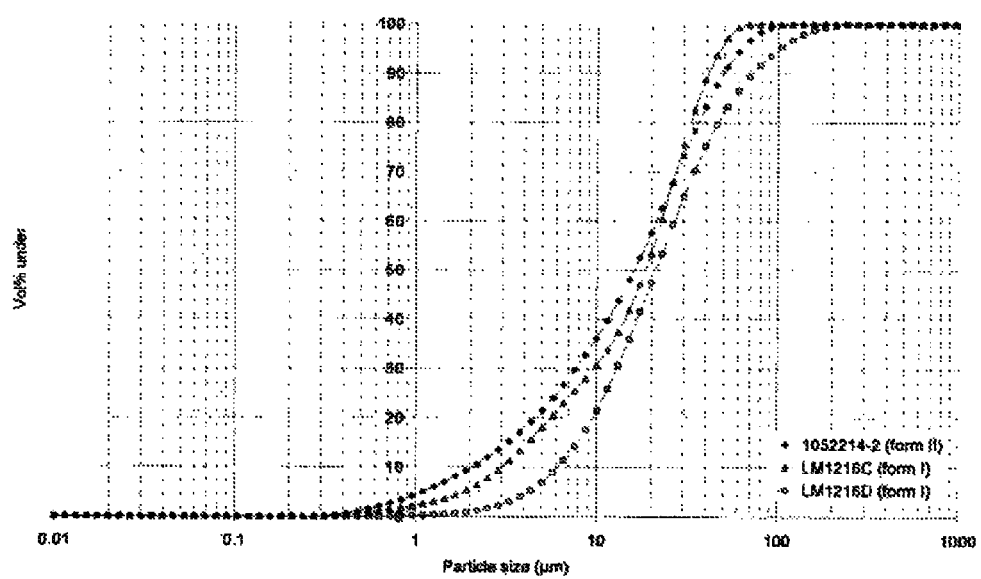

For comparison, a 100 microliter sample of a dispersion comprising 100 mg of crystalline Form II of asenapine hemipamoate particle fraction having a $d_{50}$ value of 16 microns, a $d_{90}$ value of 50 microns, and a $d_{10}$ value of 2 microns, dispersed in 1 mL of a polysorbate 80 solution, as described above was studied under the same conditions and dissolution medium used to study the sample containing crystalline Form I of asenapine hemipamoate. The results of this study are shown in the lower trace of FIG. 8a. The results presented in FIG. 8a indicate that the rate of dissolution observed for crystalline Form I of asenapine hemipamoate is significantly higher under the same conditions in comparison with that observed for crystalline Form II of asenapine hemipamoate. These results demonstrate that a formulation comprising crystalline Form I of asenapine hemipamoate is unacceptable for depot administration. FIG. 8b presents the classification characteristics of the particle fraction used in the studies described above.

The above description of the invention is intended to be illustrative and not limiting. Various changes or modifications in the embodiments described herein may occur to those skilled in the art. These changes can be made without departing from the scope or spirit of the invention

What is claimed is:

1. A pharmaceutical formulation comprising an aqueous suspension of particulate, crystalline asenapine hemipamoate exhibiting XRPD diffraction peaks at °2-theta of 11.9, 16.5, 18.8, 19.4 and 23.4, wherein the asenapine hemipamoate is present in the formulation in a concentration in excess of at least about 10 mg/mL.

2. The formulation of claim 1 wherein the formulation comprises a phosphate buffer and asenapine is present in excess of at least about 100 mg/mL.

3. The formulation of claim 2 wherein the concentration of asenapine hemipamoate present is in excess of at least about 200 mg/mL.

4. The formulation of claim 3 wherein the particles of the suspended asenapine hemipamoate have a $d_{50}$-value as measured by laser diffractometry of from about 3.5 microns to about 28 microns.

5. The formulation of claim 2 further including polyethylene glycol as a dispersing agent, and wherein said formulation has a pH of about 7.0.

6. A formulation comprising:
(i) from more than about 100 mg/mL to about 300 mg/mL of particles of crystalline Form II of asenapine hemipamoate which have not been classified and as defined by the XRPD diffraction peaks in Table I, wherein the particles have a laser diffractometry $d_{50}$-value of from about 3.5 microns to about 28 microns;
(ii) water;
(iii) up to about 30 mg of polyethylene glycol/mL of water present; and
(iv) a buffer.

7. A pharmaceutical formulation comprising an aqueous suspension of particles of crystalline Form II of asenapine hemipamoate, as defined by the XRPD diffraction peaks in Table I, wherein:
(i) said particles have a laser diffractiometry $d_{50}$-value of from about 3.5 microns to about 28 microns; and
(ii) the concentration of asenapine hemipamoate present in the formulation is at least sufficient so that when a depot of the formulation is administered to a patient by IM injection in a sufficient quantity to provide a therapeutically effective plasma concentration, the plasma concentration observed is not particle-size dependent.

8. The formulation of claim 6 wherein the concentration of asenapine hemipamoate is greater than at least about 100 mg/mL.

9. The formulation of claim 6 wherein said buffer was prepared by combining: disodium hydrogen phosphate in an amount of from about 1.0 mg/mL to about 1.2 mg/mL of water present; sodium dihydrogen phosphate in an amount of about 0.5 mg/mL of water present; sodium chloride in an amount of about 7.6 mg/mL of water present; and titrating the mixture with aliquots of sodium hydroxide and phosphoric acid until the mixture attains a pH of about 7.0.

10. A depot prepared by providing an IM injection of the formulation of claim 1.

11. A depot of claim 10 which comprises a volume providing a therapeutically effective plasma concentration of asenapine for a period of either 2 weeks, 3 weeks, or 4 weeks.

12. A method of treating a CNS disease comprising administering a depot according to claim 10 to a patient.

13. The method of claim 12 wherein the disease treated is schizophrenia or a bipolar disorder.

14. An asenapine hemipamoate salt having an XRPD pattern which conforms to that of FIG. 3b.

15. A formulation adapted for depot administration comprising an asenapine hemipamoate salt having an XRPD pattern which conforms to that of FIG. 3b.

16. The formulation of claim 1 wherein said crystalline Form II of asenapine hemipamoate has an XRPD pattern which conforms to that of FIG. 3b.

* * * * *